US005147291A

United States Patent [19]

Cukier

[11] Patent Number: 5,147,291

[45] Date of Patent: Sep. 15, 1992

[54] SOUND TRANSMISSION APPARATUS FOR UNIFORMLY ADMINISTERING CHEMICAL COMPOSITION THROUGH THE SKIN

[76] Inventor: A. David Cukier, 2604 S. Bala Dr., Tempe, Ariz. 85282

[21] Appl. No.: 535,510

[22] Filed: Jun. 11, 1990

[51] Int. Cl.[5] ........ A61N 1/30

[52] U.S. Cl. ........ 604/20; 604/22; 604/290

[58] Field of Search ........ 604/20, 22, 49, 289, 604/290, 291; 128/24 AA

[56] References Cited

U.S. PATENT DOCUMENTS

| | | | |
|---|---|---|---|
| 4,657,543 | 4/1987 | Langer et al. | 604/22 |
| 4,702,732 | 10/1987 | Powers et al. | 604/20 |
| 4,767,402 | 8/1988 | Kost et al. | 604/22 |
| 5,016,615 | 5/1991 | Driller et al. | 604/20 |

*Primary Examiner*—Stephen C. Pellegrino
*Assistant Examiner*—Michael Rafa
*Attorney, Agent, or Firm*—Tod R. Nissle

[57] ABSTRACT

A method utilizing sound and an aqueous sound transmission gel to transmit minor effective amounts of an anti-inflammatory pharmaceutical agent in uniform quantities through all points in a selected area of the intact skin of the body of an individual.

2 Claims, No Drawings

SOUND TRANSMISSION APPARATUS FOR UNIFORMLY ADMINISTERING CHEMICAL COMPOSITION THROUGH THE SKIN

This invention relates to a method for introducing anti-inflammatory and other pharmaceuticals in the body of an individual.

More particularly, the invention relates to a method which utilizes sound and an aqueous sound transmission gel to transmit minor effective amounts of an anti-inflammatory pharmaceutical agent in uniform quantities through points in a selected area of the intact skin of the body of an individual.

Iontophoresis or electrophoresis is well known in the art and consists of applying a direct electric current to the body to drive ions through the skin into the body. During iontophoresis, a non-water soluble anti-inflammatory drug such as hydrocortisone is driven through the skin. The hydrocortisone is mixed in a cream or ointment which typically comprises about ten percent by weight of a cream or ointment which is placed on the skin. After the cream is applied to the skin, an electrode is positioned against the cream. While the electrode is maintained in a stationary position on the cream a galvanic current is transmitted from the cathode pole of the electrode, through the skin, and to the anode pole of the electrode.

The dangers associated with iontophoresis are suggested by the below TABLE 1: RULES FOR THE APPLICATION OF GALVANIC CURRENT.

TABLE 1

Rules for the Application of Galvanic Current

1. Caution should be used to prevent Galvanic Burns.
2. Never dispute the patient. If he complains, investigate.
3. Be careful with paralyzed patients.
4. Avoid shocks.
5. See that the pads are properly placed. (Active and Indifferent)
6. See that the Intensity Control is completely turned off before placing the pads.
7. Do not place or remove the pads while the Instrument is running.
8. Be sure to have pads thoroughly moist but not dripping wet.
9. Turn the current on and off slowly.
10. Have the patient remove enough clothing and protect the remainder from getting damp.
11. Never change poles while the current is flowing, except when testing.
12. Protect scars or wounds.
13. The skin should be thoroughly cleansed beforehand, and firm pressure should be maintained on the electrode in order to keep a perfect contact with both the gauze and the skin.
14. The active pad should be smaller than the indifferent one, and the current strength from five to fifteen milliamperes.
15. The lower the voltage the less pain, but also the less penetration.

Since hydrocortisone is not water soluble, it leaves a powder residue irritant on the skin.

It would be highly desirable to provide an improved method which would direct a drug into intact skin while avoiding the risks associated with the use of electric current and, importantly, while minimizing the amount of drug which must be utilized and while facilitating the uniform transmission of the drug into a selected area of the skin.

Therefore, it is a principal object of the invention to provide an improved method for introducing a drug through the skin into the body of an individual.

A further object of the invention is to provide an improved drug application method in which minor effective amounts of a pharmaceutical agent are transmitted into a selected area of skin of an individual without requiring that electricity pass through the skin, without requiring the large amounts of pharmaceutical be utilized, and without requiring that a non-aqueous carrier be utilized.

Another object of the invention is to provide an improved drug application method in which a pharmaceutical agent is transmitted into the skin in uniform amounts at all points within a selected area of said skin and in which transmission of the drug into the skin is automatically promoted by kneading of the skin during said transmission.

These and other, further and more specific objects and advantages of the invention will be apparent to those skilled in the art from the following detailed description thereof.

The method of the invention includes the basic steps of spreading a sound transmission gel over a selected area of the epidermis of an individual; applying a sound transmission head to the gel; continuously moving the sound transmission head; and, directing sound through the transmission head into the gel and the skin while the transmission head is continuously moved. The transmission head can be fabricated from any desired material but presently preferably is fabricated from stainless steel and has a smooth planar two inch diameter face which continuously contacts the gel. The size and shape of the face can vary as desired. The sound transmission head is connected to apparatus which generates sound having a frequency in excess of 0.5 megahertz. Ultrasonic transducers which convert electric energy into ultrasonic waves are well known in the art as a means for producing sound having frequencies in excess of 0.5 megahertz and will not be described herein.

In order to facilitate the use of the transmission head, the composition and properties of the sound transmission gel are critical and are described below.

The speed of sound through a material depends on the density and compressibility of the material. Density is the amount of material per unit volume. Compressibility indicates how easily a substance can be compacted into a smaller space. The denser a material is and the greater the compressibility of the material, the slower is the speed of sound traveling through the material.

The speed of sound through the gel utilized in the invention is important. If the speed of sound is too slow, then the sound waves are less effective in carrying an anti-inflammatory drug into the skin. Since increasing density decreases the speed of sound, a gel with a low density is desired. Another reason a gel with a low density is desired is that a material with a high density also tends to impede the movement of a drug through the gel and into the skin. On the other hand, if the density and viscosity of the gel are too low, the gel disperses over the skin. If the density or viscosity of the gel are too great, the gel impedes movement of the sound transmitting head over the skin. Continuous movement of the sound transmitting head for a period of time in excess of four minutes, preferably four to ten minutes, is crucial in obtaining the uniform application of the drug over an area of the skin which is greater than the area of the contact face of the sound transmission head. The density of the gel is in the range of 0.9 to 1.75 grams per cubic centimeter, preferably 1.0 to 1.2 grams per cubic centimeter. The viscosity of the gel at a room temperature of 76° F. is in the range of 100,000 to 250,000 CPS (centipoise) preferably 125,000 to 200,000 CPS. The viscosity of the gel decreases after the gel is applied to the skin because the gel absorbs heat from the skin.

The density and compressibility of the gel are such that the speed of sound through the gel is in excess of 1,000 meters per second and is preferably greater then 1,250 meters per second and is less than about 3,000 meters per second. The speed of movement of the sound through the gel, along with the frequency and wavelength of the sound, play an important part in carrying the anti-inflammatory drug or other drug from the gel into and through the skin. As the frequency of sound waves increases, the wavelength of the waves decreases. Higher frequency sound waves are better able to penetrate and travel through the sound transmission gel and the skin. Sound waves with a frequency in excess of 0.5 megahertz, preferably 0.7 to 3.0 megahertz, are utilized in the practice of the invention. The coupling efficiency of the gel is 90% or more, perferably 95% or more. As used herein, the term "coupling efficiency" indicates the amount of sound transmitted through a gel. A 95% coupling efficiency indicates that 5% of the sound is absorbed by a gel as sound passes through the gel.

The semi-solid colloid aqueous gel utilized in the invention is a disperse system consisting of a high-molecular weight compound in very close association with water. The gel can be elastic and jelly-like (as gelatin) or more or less rigid (as silica gel). As used herein, the high-molecular weight compound can consist of one or more polymers. A polymer is a chemical compound of which each molecule is made up of two or more simpler molecules strung together. Examples of polymers are cellulose, lignin, starch, polyethylene, rubber, and water soluble acrylic resins like Carbopol 940. As used herein, the high-molecular weight compound can also consist of or include a natural thickener such as xanthan and gum or consist of other materials which when combined with water form a semi-solid apparently homogeneous colloid which is in a more solid form than a sol. The colloid can be formed by coagulation of a sol in various ways such as by cooling, by evaporation, or by precipitation with an electrolyte. The aqueous nature of the gel is important because water is non-toxic to the skin, has a desirable pH in the range of 6.0 to 7.3, and consequently, is an excellent carrier for an anti-inflammatory or other drug. It is therefore highly desirable that the anti-inflammatory or chemical compound be water soluble and be sufficiently potent to require that only small amounts of the drug be added to the aqueous solution. If a drug or pharmaceutical agent is not water soluble, when the drug is added to the gel in powder form, the powder tends to significantly attenuate sound waves passing through the gel and to significantly reduce the effectiveness of the sound transmission method of the invention. This attenuation occurs because powder and gel typically have different densities. When sound waves traveling in one medium strike another medium some of the sound is reflected. The remainder travels into the new medium. This occurs, for example, when sound traveling through air contacts a brick wall. If the sound waves travel at about the same speed in both materials and both materials have about the same density, then only a small portion of the sound is reflected, and most of the sound travels into the new medium. When the speed of sound is greatly different in the two mediums and the densities of the mediums are quite different, then most of the sound is reflected. This is why a powder or other form of drug which is not water soluble ordinarily is to be avoided should not be combined with the aqueous sound transmission gel of the invention. The presently preferred anti-inflammatory drug utilized in the invention is dexamethasone disodium phosphate. Dexamethasone disodium phosphate is water soluble at room temperature, and only relatively small amounts need to be incorporated into the aqueous gel utilized in the invention. The gel includes 0.1% to 2.0% by weight, preferably 0.2% to 0.8% by weight, of dexamethasone disodium phosphate. Lidocaine, an anesthetic, can be incorporated in the gel in a concentration in the range of one to ten milligrams per milliliter, preferably in a concentration in the range of three to five mg/ml of gel.

The following examples are presented, not by way of limitation of the scope of the invention, but to illustrate to those skilled in the art the practice of the various of the presently preferred embodiments of the invention and to distinguish the invention from the prior art.

EXAMPLE 1

A gel was prepared by combining xanthan with water to form a rigid silica like gel. 0.4% by weight dexamethasone disodium phosphate was mixed in the gel. The gel had a density of 1.05 grams per cubic centimeter, a pH of 6.8, a viscosity of 150,000 CPS at 76° F., transmitted sound at about 1,500 meters per second, and appeared to the human eye to be a homogeneous substance. When the gel was applied to the skin of an individual, heat absorbed from the skin reduced the viscosity of the gel. The gel had a coupling efficiency of 90%+.

EXAMPLE 2

Two hundred ml of boiling water were mixed in a beaker with 13.5 grams of Carbopol 940. During the mixing the bottom of the beaker was positioned over and in contact with a reservoir of boiling water. The water—Carbopol 940 was mixed for about ten minutes until a smooth gel was formed. The beaker was removed from above the boiling water reservoir and the gel was permitted to cool, was covered with plastic wrap, and was permitted to sit for twenty-four hours so that the Carbopol would hydrate.

After the gel sat for twenty-four hours, one hundred ml of PEG 400 and 83 ml of water were mixed for about ten minutes with the gel to form a smooth gel mixture. After the smooth gel mixture was formed, another 600 ml of water was mixed into the gel mixture and the gel mixture stirred until the additional water had been uniformly dispersed in the gel.

0.3 ml of blue food coloring was stirred into the gel.

3.3 ml treithanolamine was added to 12 ml of water. This mixture was then added to the gel to cross link the $H_2O$ to the carbopol and stiffen the gel.

8.0 grams of dexamethasone disodium phosphate was mixed into the gel. The pH of the gel was about 6.7. The coupling efficiency of the gel was about 95%.

The gel had a density of 1.07 gm/cm3, a pH in the range of 6.5 to 6.9, a viscosity in the range of 130,000 to 190,000 CPS (Brookfield Viscometer, Model RVT, spindle T-C, 2.5 RPM), an acoustic impedance of about 1.6 (1.5 $gm/cm^2$ sec.), transmitted sound at about 1,500 meters per second, and appeared to the human eye to be a homogeneous substance.

EXAMPLE 3

A gel is made in accordance with the process described in EXAMPLE 2, except that 100 grams of a gelatin is utilized in place of the PEG 400 and carbopol 940 and 600 ml of ethyl alcohol is substituted for 600 ml of water.

EXAMPLE 4

A 42 year old male subject, five feet eleven inches tall, weighing 150 pounds, had complained of pain and inflammation of the lower back muscles. A quantity of the gel of EXAMPLE 2 was spread over the skin of the lower back of the male subject. The skin was intact and did not have any cuts or abrasions. The area of skin covered by the gel was about one foot by one foot. The layer of gel was about one sixteenth of an inch thick. A round stainless steel sound transmission member was placed on the gel. The sound transmission member had a circular, planar, sound transmission surface approximately two inches in diameter. The sound transmission surface was maintained in contact with the gel layer while the sound transmission member was continuously moved over the gel layer and lower back for five minutes. The viscosity of the gel decreased as the gel was warmed by the skin and by the movement of the sound transmission member. The penetration of ions into the skin caused the temperature of the skin to increase. The sound transmission member completely passed off of and moved back over each area of the back approximately the same number of times to insure uniform application of the drug in the skin. The sound transmission member was gently pressed against the gel and the skin to gently knead or depress each area of skin which the transmission member moved over. The kneading or massaging stimulated and relaxed the muscles beneath the skin to facilitate blood circulation and the dissipation of the anti-inflammatory drug in the body of the male subject. The kneading also promoted warming of the skin, as did transmission of the dexamethasone disodium phosphate into the skin. It was possible to carefully move the sound transmission head over the skin without gently kneading or massaging the skin. Such a non-massaging movement of the sound transmission head was not preferred and was avoided. The sound transmission head was connected to apparatus which caused sound waves having a frequency of two megahertz to be transmitted from the steel transmission member through the gel and into the intact skin of the male subject while the transmission head was continuously moved over the gel during said five minute period. At the end of the five minute period, the male subject experienced a noticeable decrease in the pain and inflammation of the lower back.

EXAMPLE 5

The gel of EXAMPLE 1 is prepared, except only 0.2% by weight dexamethasone disodium phosphate is mixed in the gel.

EXAMPLE 6

The treatment described in EXAMPLE 4 is utilized, except the gel of EXAMPLE 5 is utilized in place of the gel of EXAMPLE 2. Similar results are obtained.

EXAMPLE 7

The gel of EXAMPLE 1 is prepared, except 2.0% by weight of dexamethasone disodium phosphate is mixed in the gel instead of only 0.4% by weight of dexamethasone sodium phosphate.

EXAMPLE 8

The treatment described in EXAMPLE 4 is utilized, except the gel of EXAMPLE 7 is utilized and the sound transmission head is moved over the subject's back for eight minutes instead of five minutes. Similar results are obtained.

EXAMPLE 9

The treatment described in EXAMPLE 4 is utilized, except that the transmission head is moved over the subject's back for ten minutes instead of five minutes. Similar results are obtained.

EXAMPLE 10

The treatment described in EXAMPLE 4 is utilized, except that the frequency of sound waves transmitted by the transmission head is 0.7 megahertz instead of two megahertz. Similar results are obtained.

EXAMPLE 11

The gel of EXAMPLE 1 is prepared, except that in addition to the dexamethasone disodium phosphate, lidocaine is mixed with the gel in a concentration of four milligrams per milliliter of gel.

EXAMPLE 12

The treatment described in EXAMPLE 4 is utilized, except the gel of EXAMPLE 11 is utilized in place of the gel of EXAMPLE 2. Similar results are obtained except the male subject experienced a greater reduction in muscle ache and pain.

EXAMPLE 13

The gel of EXAMPLE 1 was prepared, except dexamethasone disodium phosphate was not mixed in the gel.

EXAMPLE 14

The treatment procedure described in EXAMPLE 4 is utilized. The gel of EXAMPLE 13 is utilized in place of the gel of EXAMPLE 2. The male subject does not experience a noticeable decrease in the pain and inflammation of the lower back at the end of the five minute period.

Having described my invention in such terms as to enable those skilled in the art to understand and practise it, and having identified the presently preferred embodiments thereof, I Claim:

1. A method of uniformly introducing an anti-inflammatory drug at selected points in an area of intact skin, said method including the steps of (a) applying a layer of an aqueous high molecular weight semi-solid sound transmission gel to a selected area of intact skin, said gel (i) including a water soluble anti-inflammatory chemical compound in a concentration in the range of 0.1% to 1.0% by weight, (ii) transmitting sound waves at a speed in the range of 1,200 to 1,700 meters per second, (iii) having a density in the range of 1.01 to 1.5 grams per cubic centimeter, (iv) having a viscosity in the range of 120,000 to 200,000 centipoise at an ambient temperature of 76° F., said viscosity of said gel decreasing when said gel is warmed by the skin of an individual, and (v) having a pH in the range of 6.0 to 7.3;

(b) placing a sound transmitting head over said selected area of skin, said head including a smooth face contacting said gel intermediate said sound transmitting head and a portion of said selected area of skin;

(c) continuously moving for a period of time greater than four minutes said sound transmitting head over said points in said selected area of skin to knead said skin while maintaining contact between said face and said gel; and, (d) directing sound waves from said head through said gel into said skin while said transmitting head is continuously moved over said selected area of skin, said sound waves having a frequency greater than 0.5 megahertz and driving said chemical compound into said skin; completely off of and moving back over each of said points a generally equivalent number of times to insure that a substantially uniform amount of chemical compound enters the skin at each of said points, the introduction of said anti-inflammatory chemical compound into the skin with said sound transmitting head causing the warming of said skin to reduce the viscosity of said gel.

2. The method of claim 1 wherein said chemical compound is dexamethasone disodium phosphate.

* * * * *